United States Patent [19]
Brinegar et al.

[11] Patent Number: 5,219,746
[45] Date of Patent: Jun. 15, 1993

[54] ICE-MEDIATED INTRODUCTION OF SUBSTANCES INTO BIOLOGICAL MATERIAL

[76] Inventors: Chris Brinegar, 587 Locksley Rd., Boulder Creek, Calif. 95006; James Gilmore; Michael Johnson, both of 6385 Camino Verde Dr., San Jose, Calif. 95119; Nigel Walker, 5385 Broadway #103, Oakland, Calif. 94618

[21] Appl. No.: 863,356

[22] Filed: Mar. 31, 1992

Related U.S. Application Data

[63] Continuation-in-part of Ser. No. 555,727, Jul. 19, 1990, abandoned.

[51] Int. Cl.⁵ .................... C12N 15/87; C12N 15/89; C12N 15/90
[52] U.S. Cl. ............................. 435/172.3; 435/172.1; 435/240.4; 935/52; 935/53; 935/85; 239/14.2
[58] Field of Search ............... 435/172.1, 172.3, 240.4; 935/85

[56] References Cited

U.S. PATENT DOCUMENTS 4,945,050  7/1990  Sanford et al. ................... 435/240.4

FOREIGN PATENT DOCUMENTS

| | | |
|---|---|---|
| 0270356A2 | 12/1987 | European Pat. Off. . |
| 87310612.4 | 12/1987 | European Pat. Off. . |
| 0301749 | 7/1988 | European Pat. Off. . |
| 88306613.6 | 7/1988 | European Pat. Off. . |
| 0331855A2 | 9/1988 | European Pat. Off. . |
| 88402481.1 | 9/1988 | European Pat. Off. . |

OTHER PUBLICATIONS

Sanford et al. 1987 Particulate Science and Technology 5:27–37.
Klein et al. 1987, Science, 327: 70–73.
Criston et al. 1989 Proc. Natl. Acad. Sci. USA 86:7500–7504.
Potrykus 1990 (June) Bio/Technology 8:535–542.
Biolistic Particle Delivery Systems, Bibliography, Bio-Rad Genetic Systems News.
Transform Virtually Anything!, Bio-Radiations; A Life Science Research Products Newsletters; 1991; No. 80.
S. A. Johnston, M. Riedy, M. J. DeVit, J. C. Sanfort, S. McElligott and R. S. Williams; Plant; In Vitro Cellular & Development Biology; vol. 27P, No. 1; 1990–1991.
S. A. Johnston; Biolistic Transformation: Microbes to Mice; Nature; vol. 346: pp. 776–777 Aug. 23, 1990.
Richard M. Baldarelli and Judity A. Lengyel; Transient Expression of DNA after Ballistic Introduction into Drosophila Embryos; Nucleic Acids Research, vol. 18: No. 19: pp. 5903–5904; Aug. 27, 1990.
Karen L. Kindle, Rogene A. Schnell, Emilio Fernandez and Paul A. Lefebvre; Stable Nuclear Transformation of Chlamydomonas Using the Chlamydomonas Gene for Nitrate Reductase; The Journal of Cell Biology, vol. 109 (No. 6, Pt 1) p. 2589; Dec. 1989.
Carole Gan; Gene Gun Accelerates DNA-Coated Particles to Transform Intact Cells; The Scientist, Sep. 18, 1989, p. 25.
Roger Segelken; $2.28 Million Agreement Transfers Gene Gun Technology to DuPont; Cornell Agriculture & Life Sciences News; Sep. 1989, p. 7.
John C. Sanford: The Biolistic Process; Reviews, Dec. 1988, vol. 6 pp. 299–302.

*Primary Examiner*—Elizabeth C. Weimar
*Assistant Examiner*—P. R. Moody
*Attorney, Agent, or Firm*—Limbach & Limbach

[57] ABSTRACT

Methods and apparatus for the introduction of foreign substances, such as recombinant DNA, into living cell interiors is disclosed. The desired substance to be introduced is dissolved or suspended in water or another suitable liquid to form a solution which is then nebulized and frozen to produce ice particles. These ice particles are accelerated toward and impact upon a target tissue where some of the particles impregnate at least some cells in the target tissue without killing the cells. Following impregnation, the ice particles melt, leaving behind the desired substance in the protoplasm of the bombarded cell.

12 Claims, 3 Drawing Sheets

ICE-MEDIATED INTRODUCTION OF SUBSTANCES INTO BIOLOGICAL MATERIAL

This ia a continuation-in-part of co-pending application Ser. No. 07/555,727 filed on Jul. 19, 1990, now abandoned.

FIELD OF THE INVENTION

This invention relates generally to the non-lethal introduction of foreign substances into the interiors of living cells, and more specifically to the transformation of living cells by the introduction of foreign genes.

BACKGROUND OF THE INVENTION

A variety of techniques are known for the introduction of foreign substances, particularly DNA, into the interiors of living cells without killing those same cells. One class of techniques involves manipulating the cell membrane to make it permeable to DNA molecules. For instance, in bacteria, yeasts and protoplasts of higher plant cells, treatments with chemicals or heat can be used to make the cell membranes "leaky," thereby permitting a desired gene or genes (often integrated in small loops of DNA called plasmids) to be taken up into the cell.

In another class of techniques, DNA is physically injected into living cells, particularly ova, of various animal species. DNA can also be taken up by electrically stimulated cells in a process known as electroporation. In another procedure, the cell is made permeable using a precision laser to burn holes into the cell membrane.

Yet another type of gene introduction can be accomplished using naturally occurring processes. Gene transfer is accomplished by infecting certain susceptible dicotyledonous plant species with a particular bacterial species of the genus Agrobacterium. The bacterium possesses plasmids as a part of its normal complement of DNA. Upon infection, the bacterium is capable of transferring portions of these plasmids to the cells of the plant it infects. Thus, it is possible to accomplish the introduction of specifically desired genes by engineering Agrobacterium species with recombinant plasmids possessing the desired gene and subsequently infecting a susceptible plant with the engineered bacterium.

Most recently, another type of gene introduction method has been described. Termed "microprojectile bombardment" or "biolistics," this technique involves coating tiny metal spheres with desired DNA, and then accelerating these projectiles into tissues. Acceleration is generally achieved by shooting the microprojectiles from a gun aimed at the target tissue. Once inside the cell, the foreign DNA detaches from the metal sphere and, in certain of the bombarded cells, is incorporated into the host cell's DNA. See, e.g., Sanford, J. C., "The biolistic process," *Trends in Biotechnology*, 6:299-302 (1988); Klein, T. et al. "Stable genetic transformation of intact Nicotiana cells by the particle bombardment process," Proc. Nat. Acad. Sci. USA 85:8502-8505 (1988); E.P. Application, Ser. No. 87310612.4; E.P. Application, Ser. No. 88306613.6; and E.P. Application, Ser. No. 88402481.1.

Unfortunately, each of the above methods has distinct disadvantages. The methods may be taxonomically limited, such as with Agrobacterium-based methods. Membrane permeability methods have limited application with organisms presenting cell walls. Electroporation methods achieve only a very low efficiency of stable transformation. Several methods, such as microinjection and laser-mediated cell membrane manipulation are extremely tedious, time consuming and require highly specialized equipment.

Although the biolistics approach avoids some of these drawbacks, the design and composition of the microprojectiles presents disadvantages unique to the method. For instance, metal microprojectiles can easily clump into larger aggregates that, upon impact, can cause significant cell damage. The type of substances that can be introduced into the cell is limited to negatively charged molecules such as DNA and RNA. The amount of DNA or RNA carried with each microprojectile cannot be easily controlled or measured. The long-term chemical and physical effects of the metal microprojectiles inside the cell are unknown. Finally, the use of metallic agents requires considerable preparation time, thus affecting the economic efficiency of the method.

SUMMARY OF THE INVENTION

The foregoing and other problems associated with known methods of introducing substances into cells are overcome by the present invention. According to the present invention, a desired substance to be introduced into a cell is added to a desired liquid capable of dissolving, suspending or encapsulating the substance. For the purposes of the specification and claims, solution will be defined to include liquids in which the desired substance is either dissolved or suspended or in part both. The solution is then used to make ice particles that contain the desired substance. These ice particles are then accelerated toward a target tissue whereby at least some of the particles impact upon and enter at least some cells in the target tissue without killing the cells. Once inside the cell, these ice particles then melt, leaving behind the desired substance in the protoplasm of the bombarded cell.

The method of the present invention is superior to existing methods in that it provides a way to introduce not only DNA and RNA, but also non-negatively charged substances, including but not limited to proteins, enzymes, protein/DNA complexes, bacteria, viruses, hormones, etc. into living cells. The ability to introduce enzymes and proteins simultaneously with DNA and RNA may materially improve DNA/RNA viability rates as well as transformation rates of individual cells. Further, the ice projectile ceases to exist after it melts, thereby leaving no residue that may poison or otherwise contaminate the bombarded cell at some future time. Because the ice projectiles are produced from a solution of known concentrations, it is easy to control and predict the amount of DNA or other substance to be delivered to a particular cell. Also, ice particles may be less likely to clump and thus less likely to cause fatal trauma to bombarded cells. Further, it is possible, for a particle of a given diameter, to incorporate more of the desired substance than can be incorporated onto the surface of a metal particle.

It is therefore an object of the present invention to introduce a variety of substances into biological material in a non-lethal manner.

It is another object of the present invention to accomplish substance introduction with a minimal amount of trauma to the bombarded cell.

It is a further object of the present invention to accomplish substance introduction without producing a by-product that may in time deleteriously affect the functioning of the bombarded cell.

It is yet another object to provide a method of introducing foreign substances into cells that is both efficient and cost-effective.

A further object of the present invention is to provide a method of substance introduction that is efficacious for a wide variety of different species and tissue types.

It is still another object of the present invention to provide a method of introducing DNA into cells in which the rate of transformation is high.

Another object of the present invention is to provide a simple and cost effective method for generating ice particles of an appropriate size range containing the desired substance.

Still another object of the present invention is to provide an apparatus for the production of ice particles.

A further object of the present invention is to provide a simple, self-contained apparatus for accelerating ice particles toward a target tissue that is inexpensive to construct and easy to operate.

These and other objects of the present invention will be more readily understood upon consideration of the following detailed description of embodiments of the invention and the drawings.

DETAILED DESCRIPTION OF THE INVENTION

Figures 1A, 1B:
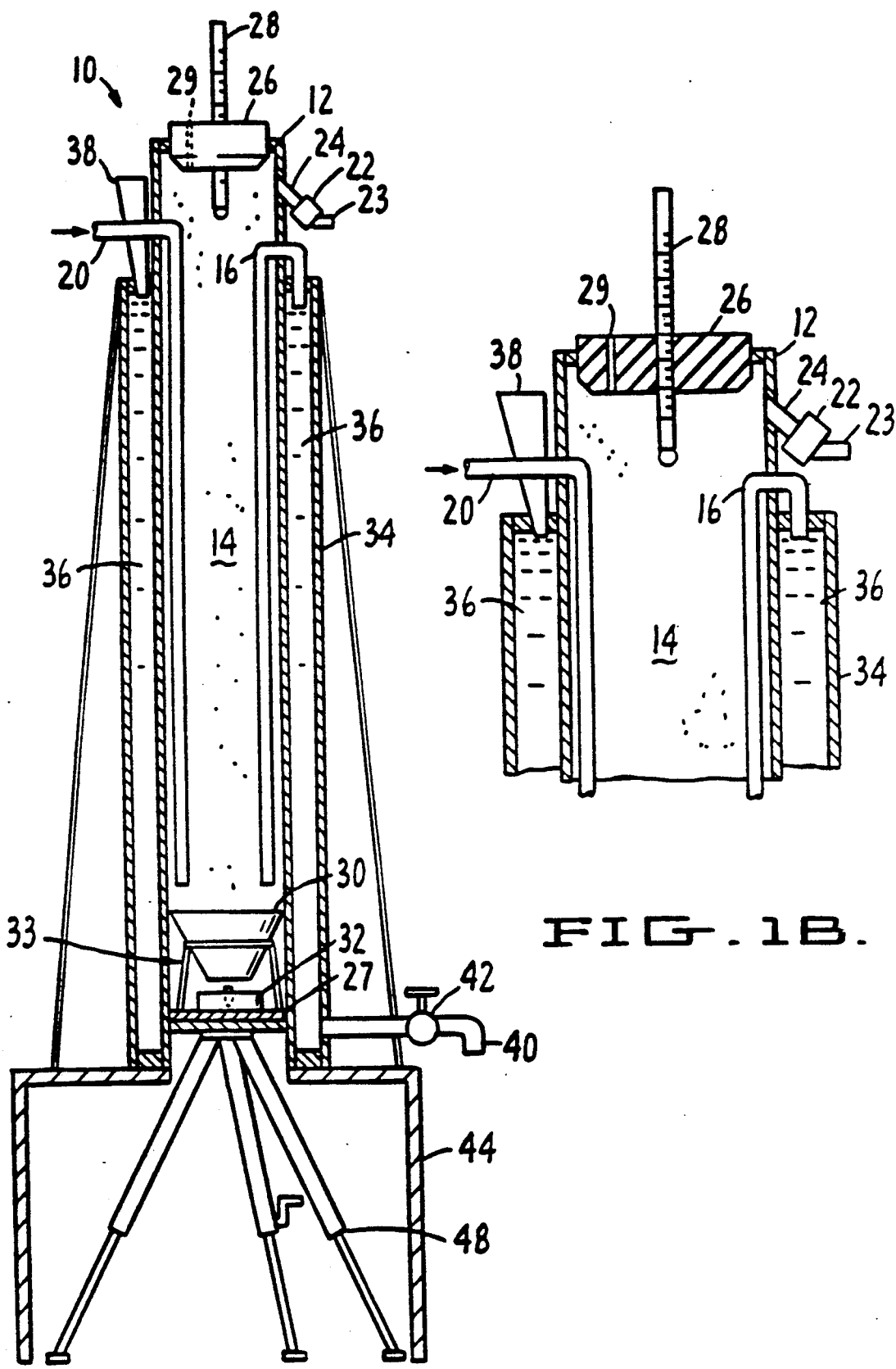
FIG. 1A is a view in cross-section of the ice particle generator of the present invention.
FIG. 1B is a view in cross-section of an apical portion of the ice particle generator of the present invention.
Figure 1C:
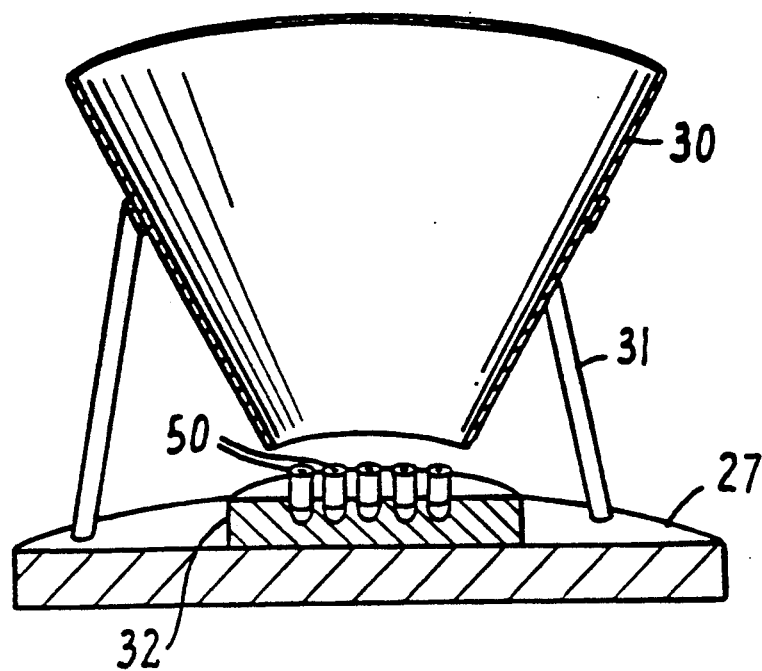
FIG. 1C is a view in cross-section of a funnel assembly of the present invention.
Figures 2A, 2B:
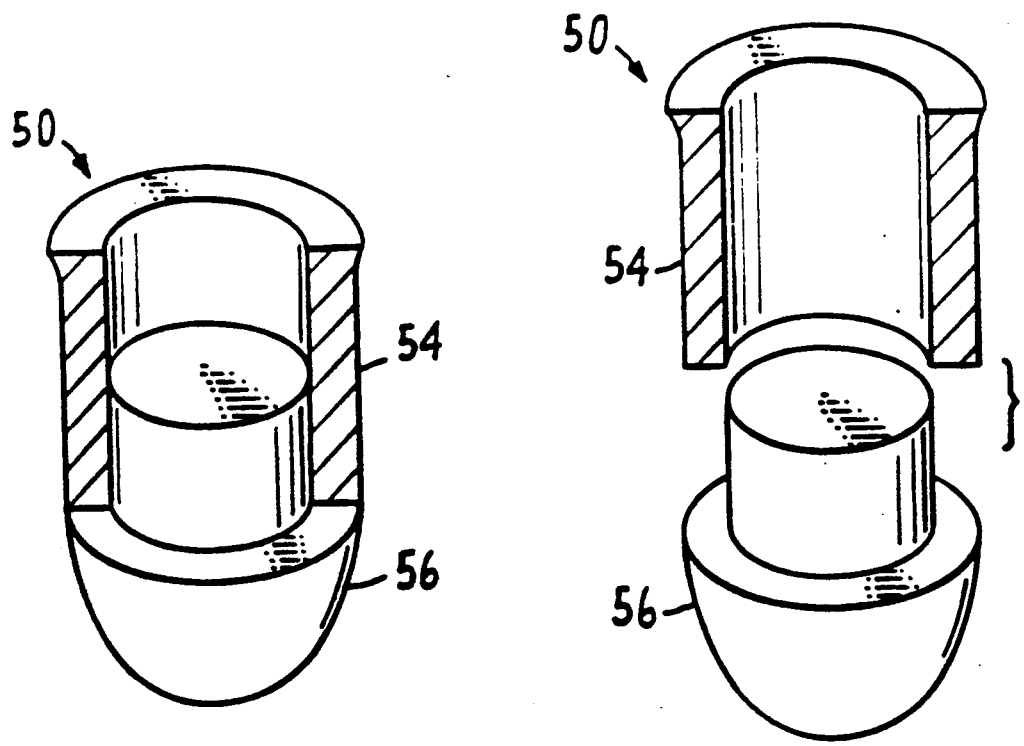
FIG. 2A is a cutaway view in perspective of the pellet of the present invention.
FIG. 2B is an exploded cutaway view in perspective of the pellet of the present invention.
Figure 3A:
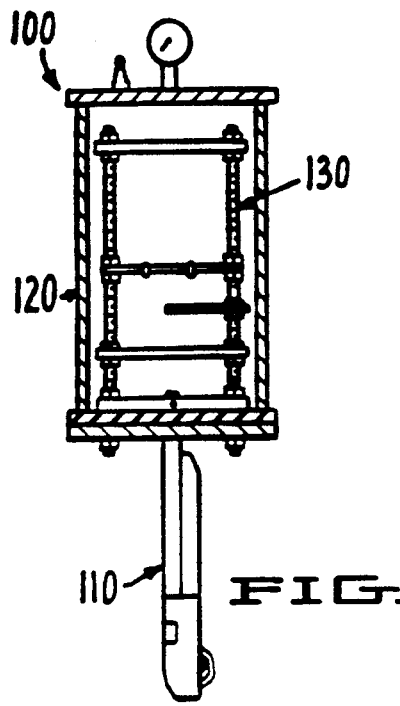
FIG. 3A is a view in cross-section of the ice particle accelerator of the present invention.
Figure 3B:
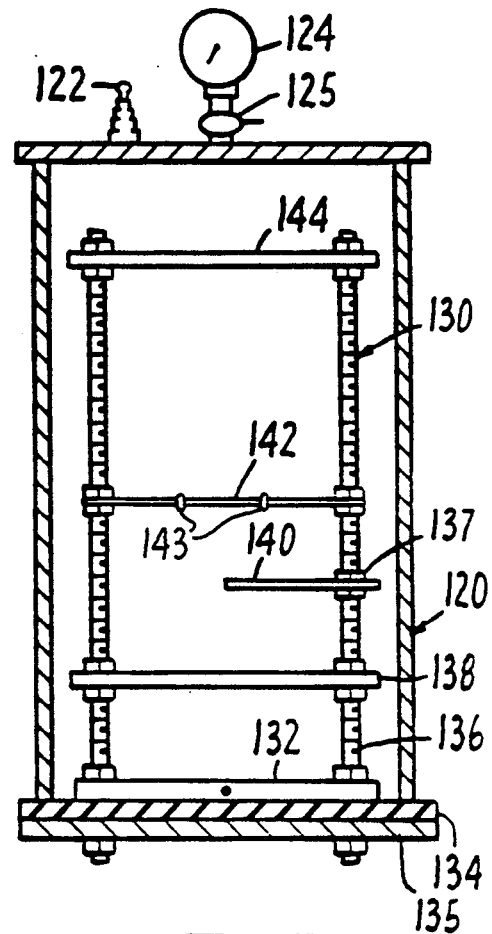
FIG. 3B is a view in cross-section of the vacuum chamber portion of the ice particle accelerator of the present invention.
Figure 3C:
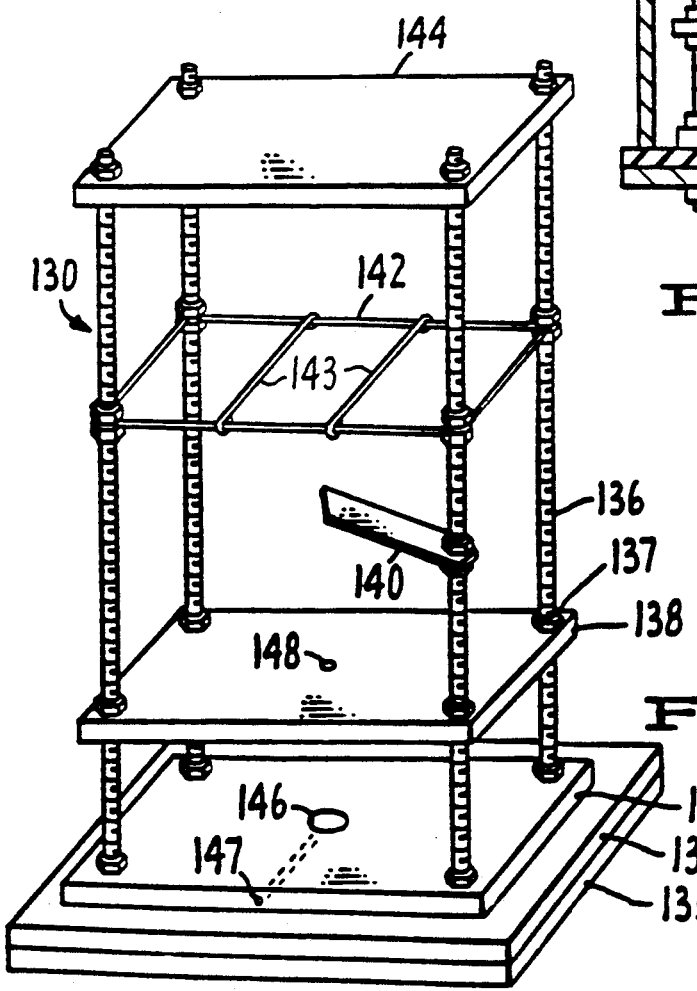
FIG. 3C is a schematic view in perspective of the support apparatus within the vacuum chamber of the present invention.

Referring now to FIG. 1, the ice particle generator of the present invention Will now be described. The generator 10 is comprised of an inner shell 12 which defines a freezing chamber 14. The freezing chamber 14 is provided with a gas feed line 20 from a regulated nitrogen tank. It is also provided with a nitrogen gas recycling line 16 which leads from coolant chamber 36.

The freezing chamber 14 is further provided with a nebulizer 22 for dispersing the solution into a mist of very fine particles and a mist feed line 24 permitting the mist to enter the freezing chamber 14. The nebulizer 22 is attached externally to a gas feed line 23 that is attached a tank of compressed nitrogen or other substantially inert gas. The nebulizer should be capable of forming mist particles that upon freezing are of an average diameter of 1 micron. One such suitable nebulizer is produced by De Vibliss Company, model no. 644.

The freezing chamber 14 is closed above by emplacement of a stopper 26 at the apex and by an end segment 27 at the base of the inner shell 12. The stopper 26 is provided with a thermometer 28 for gauging the temperature of the freezing chamber, and is provided with a vent hole 29. Placed upon the end segment 27, at the base of the freezing chamber, there is provided a pellet holder 32 in which are emplaced pellets 50. Above the pellet holder 32 is placed a funnel assembly 33, comprising a funnel 30, supported by a three-legged ring stand 31, for collecting the ice particles formed from the mist produced by nebulizer 22 and for directing the particles into the pellets 50.

The generator 10 further comprises an outer shell 34 positioned to surround the inner shell 12 for substantially much of its length. The position of the outer shell 34 with respect to the inner shell 12 defines an coolant chamber 36. The coolant chamber 36 is provided with a coolant feed 38 and a coolant drain 40, which is provided with a flow valve 42.

The inner and outer shells 12 and 34 sit atop a support 44. End segment 27 is supported by a vertically adjustable tripod 48 which allows the insertion, height adjustment, and removal of end segment 27, pellet holder 32, three-legged ring stand 31, funnel 30 and pellets 50.

The inner and outer shells 12 and 34 may be composed of any suitable material resistant to cracking or other degradation that may result from rapid temperature changes. Suitable materials include galvanized steel, stainless steel, aluminum, sheet metal, copper and other materials such as ceramics and plastics. Metals are preferred because they are inexpensive and easy to form. The stopper 26 is preferably composed of rubber. The collection funnel 30 is preferably composed of some smooth-surface polymer plastic or glass resistant to rapid temperature changes. The pellet holder 32 is preferably composed of a foamed rubber or polymer plastic.

Referring now to FIG. 2, an air rifle pellet of the present invention will now be described. A suitable air rifle pellet is produced by Prometheus Company. Pellet 50 is comprised of two parts, a core 56 comprised of aluminum having a broad rounded base which has been filed flat and a narrower projecting columnar portion, and a casing 54 comprised of plastic that is configured to be received over the columnar portion of core 56. The pointed or curved base of core 56 has been filed flat in order to permit the casing 54 to be loaded and fired from gun 110 in a position that is backwards relative to its intended orientation.

Alternatively, the casing 54, may be removed from the core and sealed on one end. Sealing may be accomplished by any appropriate method such as taping, gluing, heat sealing, etc.

Production of ice particles using the generator 10 described above is accomplished as follows. First, the desired substance to be introduced into the target cell must be selected. In the case of many substances such as proteins, enzymes, etc., all that is required is the dilution of the substance in an appropriate, liquid to a desired concentration. Water is preferred. Where transformation of the cell is desired, an appropriate vector capable of cell transformation is selected. The vector is then manipulated to include the desired gene or genes to be integrated into the genome of the target cells. Once manipulation is complete, the vector can be multiplied and isolated by various techniques that are well known in the art and then dissolved and diluted in a solution to a desired concentration. This solution is then maintained under conditions sufficient to ensure that the biological properties of the selected substance are maintained.

Prior to ice particle generation, the generator 10 is conditioned as follows. Pellets 50 are placed in the funnel assembly 33 by securing pellets 50 in the pellet holder 32. The pellet holder 32 is then placed beneath the collection funnel 30 (which is supported by the three-legged ring stand 31) atop end segment 27. The end segment 27 is then raised into the bottom of the freezing chamber 14 by means of tripod 48. Stopper 26 with thermometer 28 should be securely inserted into the upper end of freezing chamber 14.

Once the generator 10 is assembled, the production of ice particles may begin. The freezing chamber 14 is flushed With compressed nitrogen via feed gas line 20. It is preferred to feed the nitrogen into the freezing chamber 14 at about 5 psi for a period of two minutes. Flushing with nitrogen gas ensures that all water vapor has been evacuated from freezing chamber 14 via vent 29. Failure to rid chamber 14 of Water vapor may result in the formation of unwanted ice particles that can contaminate the desired ice particles later to be generated.

Following chamber flushing, coolant is added to the coolant chamber 36 through coolant feed 38 in an amount sufficient to fill the chamber. This will cause the temperature within the freezing chamber to drop. The preferred coolant is liquid nitrogen. A sufficient amount of cooling has taken place when the thermometer 28 records a temperature of 5° C. below the freezing point at the desired length. Cooling efficiency is increased when gaseous nitrogen that boils off coolant chamber 36 is transferred into the bottom of freezing chamber 14 via gas recycling line 16.

Once the freezing chamber 14 has reached the proper temperature, the nebulizer 22 is filled with the sample solution prepared previously. In the De Vibliss nebulizer disclosed above, it is preferred to add approximately 5-7 ml of the desired solution. At this time, nitrogen gas is fed into nebulizer 22 through feed 23 at about 5 psi. This begins mist formation, with the mist entering the freezing chamber 36 via mist feed line 24.

As the mist particles fall through freezing chamber 14, they freeze and are collected in collection funnel 30, which directs the particles into the pellets 50. Ice particles collect in pellets 50, largely under the influence of gravity. Material comprised solely of such free frozen granules is referred to as "powder." A certain proportion of the ice particles generated will collect on the sides of funnel 30. These may be scraped and packed manually. Frozen material collected in this fashion is referred to as "packed."

Generally speaking, nebulization should be carefully regulated to ensure that the biological properties of the desired substance in solution are preserved. Where transformation vectors are employed, excessive pressure or nebulization time can result in shearing of the DNA molecule, rendering the vector incapable of transforming the target cell. Thus, the pressure and length of time used to nebulize a solution containing such vectors will vary according to the fragility of the vector. Such parameters can easily be determined experimentally using techniques well known in the art, whereby fragility of the vector is generally proportional to vector size and configuration.

As an alternative to ice particle generation through nebulization, the solution containing the desired substance may be "block-frozen." The ice blocks can then be chipped or ground up and manually packed into an appropriate pellet casing.

As an alternative to nebulized particle generation, pellets containing block frozen ice can be fired intact with the particles being generated upon impact with the stopping plate 138, as can be seen in FIG. 3. As a further alternative, the solution can be block frozen in the pellet and then subjected to sonication which will generate fracture lines within the ice block, thereby causing a more efficient shattering upon impact.

Care should be taken to ensure that the sample, once frozen, does not thaw before it is used. Care should be taken to ensure that the pellets 50 containing packed block-frozen solution or ice particles are kept frozen until used. One suitable method is to pack the pellets into a suitable container, such as a block of foam plastic polymer with receptacles for receiving the pellets. The plastic block with pellets 50 can then be stored under cold conditions, such as being floated on liquid nitrogen in a covered, insulated container.

Turning now to FIG. 3, the ice particle accelerator 100 will be described. Accelerator 100 is comprised of three principal parts: a gun 110, a housing 120, an a support structure 130.

Gun 110 provides the accelerating force. the make and specifications of gun 110 will depend upon the type of pellet used. However, acceleration using chemical charges or other heat intensive methods are not compatible with ice particle acceleration in the present invention. In the methods of the present invention it is preferred to use pellets designed to be shot from air guns. Smooth bored guns are preferable over rifles in that frictional heat upon discharge is reduced resulting in a greater amount of the ice remaining frozen.

Housing 120 is configured to fit over support structure 130 to form a tight seal so that a partial vacuum can be created and maintained interior to housing 120. Housing 120 is provided With vacuum hose adapter 122 and vacuum gauge 124. The vacuum gauge 124 is provided with a three way valve 125 through which air may be reintroduced into the interior housing 120 when a vacuum is no longer required. The housing can be comprised of any convenient material that is sufficiently strong to contain a partial vacuum without structural failure. Plexiglass is preferred because it is inexpensive and easy to form.

Support structure 130 is designed to receive, position and hold the tissue sample for impact during acceleration of the ice particles. The support structure comprises a base plate 132 and a sandwich comprised of a seal 134 above and a plexiglass sheet 135 which is placed below. Base plate 132, seal 134 and sheet 135 are provided with an aperture 146 extending continuously through the two plates when joined. Aperture 146 provides an entry point into the accelerator for gun 110 which is positioned below. Base plate 132 is further provided with a bore hole 147 through which a set screw can be inserted and used to position and secure the barrel of gun 110 in proper alignment with apertures 146 and 148. The base plate 132 should be durable and strong and is comprised of metal, preferably steel.

Four rods 136 are secured to the base plate 132. The interior structure is stabilized by the addition of a structural support plate 144 which is secured to rods 136 opposite the base plate 132. The rods are threaded along their length to accommodate bolts 137 that are used to position various elements of support structure 130 that will presently be described. Just above the base plate 132 is positioned a stopping plate 138. Stopping plate 138 has a hole located at each of the four corners of the plate to allow stopping plate 138 to slide down and over the ends of rods 136. Stopping plate 138 is positioned at a desired distance from base plate 132 by resting the plate on bolts 137 that have been screwed down along rods 136 to a desired position. Once in place, stopping plate 138 is secured into place by a second set of bolts 137.

Stopping plate 138 is provided with an aperture 148 positioned on the plate so that aperture 148 is in direct vertical alignment with aperture 146. After discharge, the pellet containing the ice particles will impact at aperture 148. Aperture 148 should be small enough in diameter to stop the pellet 50 but large enough to permit the ice particles to pass and continue toward the target tissue. Stopping plate 138 is comprised of any durable material capable of sustaining repeated bullet impacts without rapid deterioration; steel is preferred.

Above stopping plate 138 is positioned a metal deflector 140. The tip of deflector 140 should be positioned over aperture 148 of stopping plate 138 so that discharged ice particles that have passed through aperture 148 go on to strike deflector 140 thereby being dispersed into smaller fragments and over a larger area. This helps to minimize the incidence of large frozen fragments that might lethally damage tissue on impact and helps to ensure that a greater area of the tissue will be impacted by the ice particles. Deflector 140 is laterally attached to one the rods 136 and may be positioned at any desired point along a rod in the same way as stopping plate 138. The deflector is a length of sterilizable material (steel is preferred) that can withstand repeated impact. It has a conical tip extended to a sharp point which further aids in dispersing ice projectiles. Use of a deflector is not required in all instances.

Above deflector 140 are positioned support wires 142. Bridging the support wires are a pair of adjustable wires 143. The adjustable wires 143 are slidable along support wires 142 so as to accommodate target material of varying size and shape. Target tissue is placed on the adjustable wires 143. It should be understood that the positions of each element of the infrastructure of support structure 130 can be adjusted relatively to one another along rods 136.

Having described the ice particle accelerator 100, the method of introducing foreign substances according to the present invention will now be described. Stopping plate 138 is secured to rods 136 at a distance from gun 110 sufficient to allow an optimum number of ice particles to be accelerated through aperture 148. Deflector 140, if desired, may then be positioned above stopping plate 138 at a sufficient distance to ensure that ice particles are scattered for impact over a large area of the target tissue. The desired target tissue is placed on adjustable wires 143 at a desired distance from gun 110 to ensure that the tissue is impacted with ice particles in a substantially non-lethal manner.

Once the supporting structure with target tissue is set up, outer housing 120 is placed over support structure 130 such that a good seal is formed between the support structure 130 and the outer housing 120. A moderate vacuum is then applied to the chamber to reduce heat of friction between the ice particles and the atmosphere. The amount of vacuum varies according to tissue type, although it is generally preferred to reduce pressure by 20 to 30 inches of mercury prior to acceleration. At this time, the temperature of the accelerator should be lowered sufficiently to ensure that the ice particles remain frozen prior to tissue impact.

A pellet 50 containing nebulized or block frozen solution containing the desired substance is retrieved from storage and loaded into the gun 110 so that the end of pellet 50 which contains the core 56 rests at the bottom of the gun chamber. This ensures that the open end of pellet 50 which contains the frozen solution will be facing toward aperture 148. After loading, the gun is discharged, thereby accelerating pellet 50 toward stopping plate 138. Pellet 50 is stopped upon impact with stopping plate 138, but the frozen solution within pellet 50 continues through aperture 148. As a general matter, impact with the stopping plate fragments the frozen solution, if block frozen, or mostly disperses the frozen solution, if nebulized, into ice particles as the pellet strikes the stopping plate.

Having passed through aperture 148, the ice particles are further dispersed as they strike deflector 140. The deflector acts to enlarge the impact zone of the ice particles on the target tissue by making the trajectories of the ice particles more oblique relative to their original paths. After passing the deflector, the ice particles travel on to and imbed in the target material. After impact, the target material may be left in place and reimpacted as desired. Once the desired number of impacts has been achieved, air is bled into the housing 120 via the three way valve 125 until pressure inside the accelerator 100 is equal to atmospheric pressure. The housing is then separated from the rubber seal 134 and the target material removed.

EXPERIMENTAL

The use of methods and apparatus of the above described invention in transforming plant tissues will now be described.

Plasmid pBI121 (obtained from CLONTECH Laboratories, Palo Alto, Calif.) was selected for the gene vector because it contains genes for the enzymes beta-glucuronidase (GUS) and neomycin phosphotransferase II (NPT II). When expressed in an organism, GUS can form an insoluble blue dye in the presence of the reagent 5-Bromo-4-Chloro-3-indolyl beta D-glucuronic acid, "X-gluc." NPT II produces an enzyme that inactivates the antibiotic kanamycin which otherwise kills normal plant cells. These genes are effectively "markers" in that their expression indicates that the cell has taken up the plasmid and the genetic information of the plasmid is being expressed. Of course, further engineering of the plasmid to include a specific desired foreign gene will be required in application of the invention described herein.

Replication of the plasmid to produce a sufficient quantity of plasmids for experimentation was accomplished by transforming competent cells of *Escherichia coli* strain JM109 (obtained from Promega, Inc.) using standard, well known methods. The transformed *E. coli* were grown to a high density in a rich liquid medium of a standard composition well known in the art for effective *E. coli* culture.

Once a sufficient volume of culture was obtained, the pBI121 plasmids were isolated from the *E. coli* cells by alkaline lysis, followed by a cesium chloride density gradient centrifugation according to procedures well known in the art. The plasmids were precipitated with ethanol and dried according to standard techniques in the art. The plasmids were then redissolved in a sterile 10 mM aqueous solution of sodium chloride to a concentration of 0.1 mg/ml. Standard Tris-EDTA buffer was not used to redissolve the plasmids in order to avoid the introduction of potentially toxic compounds into the target tissue.

The plasmid containing solution was then frozen according to the techniques set forth and described above. In instances where the ice particles are formed according to the nebulization technique of the present invention, care was taken to avoid treatment that would destroy the integrity of the plasmid and thus its ability to achieve transformation of the target tissue. Thus, it was found that nebulization pressures in excess of 5 psi and nebulization times in excess of ten minutes should be avoided when using plasmid pBI121 as the desired gene vector. Pressures and times in excess of these figures will shear substantially all the plasmid into segments too small to effect transformation.

The prepared pellets were loaded then accelerated toward the target material positioned within the ice particle accelerator according to the method described above. After this treatment, the material was incubated in a sterile container at 25° C. under a relative humidity approaching 100% to permit transformation and expression.

After incubation, the treated tissues were histochemically stained for GUS activity using "X-gluc" substrate according to the methods set forth in the manufacturer's directions. The GUS enzyme acts on the "X-gluc" substrate, resulting in an insoluble blue dye that forms crystalline deposits in transformed cells. The target tissue was allowed to incubate overnight at 37° C. in the "X-gluc" substrate, and was examined thereafter to ascertain the number of transformed cells.

EXAMPLE 1a

A comparison of the transformation efficiencies of nebulized frozen plasmids versus block frozen plasmids on corn leaves and tobacco leaves was conducted using the methods described above. The results are presented in Table I.

TABLE I

Transformation of Tissue Using Block Frozen vs. Nebulized Plasmid (pBI121)

| Tissue | Transformants per shot (average) | |
|---|---|---|
| | Block Frozen(a) | Nebulized(b) |
| Corn Leaf | 2.5 | 3.7 |
| Tobacco Leaf | 6.0 | 0.5 |

(a)10 ul. of plasmid (0.1 mg/ml)
(b)Pellets filled with nebulized plasmid powder (0.1 mg/ml)

These results show that both monocots and dicots can be transformed by the method of the present invention. Further, the efficiency of block frozen v. nebulized ice projectiles in transformation will depend on species and tissue type.

EXAMPLE 2

In this example, the effect of varying the volumetric amount of frozen plasmid solution having a standard plasmid concentration of 0.1 mg/ml was investigated. The results are set forth in Table II.

TABLE II

Transformation of Tissue Using Varying Volumes of Block Frozen Plasmid (pBI121)

| Tissue | Volume (μl) | Transformants per shot(average) |
|---|---|---|
| Corn leaf | 3 | 2.0 |
| | 10 | 6.3 |
| Tobacco Suspension cells | 20 | 23.0 |
| | 50 | 57.0 |

From the experiments, it is apparent that different types of tissue can be transformed using the method of the present invention. Further, an increase in the volume of the block frozen plasmid appears to achieve an increase in transformation rate.

EXAMPLE 3

The ice-mediated transformation method of the present invention was used to transform a preparation of tobacco suspension cells as follows.

Young leaf tissue was obtained from plants of the Wisconsins 38 cultivar of *Nicotiana tabacum* L. The leaf tissue was surface-sterilized, then transferred to Murashige-Skoog basal agar media (pH 6.0) supplemented with 0.1 mg/l 2,4-dichlorophenoxyacetic acid, 3.0 mg/l α-naphthaleneacetic acid, 0.04 mg/l $N^6$-benzylaminopurine, and 30 g/l sucrose. After a two-week dark incubation period at 25° C., the callus tissue was minced and transferred to flasks of liquid Murashige-Skoog basal media (pH 6.5) supplemented with 0.5 mg/l 2,4-dichlorophenoxyacetic acid and 20 g/l sucrose. The flasks were shaken at 55 rpm in the dark for 14 days at 25° C. Remaining pieces of intact callus tissue were removed by passing cultures through a sterile 2.5 mm mesh screen. The suspended cells (2.0 ml) were immobilized onto the surface of Whatman #1 filter paper circles (5.5 cm diameter) by gentle vacuum filtration. The filter papers were placed (cell side up) onto the surfaces of 1.5% (w/v) agar media in 5.5 cm diameter petri dishes which kept the cells moist and provided a shock-absorbing "backing" during the transformation.

Plasmid DNA used to transform the tobacco suspension cells was prepared as follows: Plasmid pBI121 (Clontech Laboratories, Palo Alto, Calif.) is 13 kilobase pairs long and contains a chimeric reporter gene having a cauliflower mosaic virus 35S promoter sequence, a β-glucuronidase (GUS) coding sequence, and a nopaline synthase terminator sequence. This construct also contains the gene for neomycin phosphotransferase (npt II) which imparts resistance to the antibiotic kanamycin. *Escherichia coli* cells (strain JM109) were transformed with pBI121 by the calcium chloride method well known in the art and grown overnight at 37° C. to stationary phase in "terrific" broth (12 g/l tryptone, 24 g/l yeast extract, 4 ml/l glycerol, 17 mM $K_2HPO_4$ and 72 mM $KH_2PO_4$) containing 50 mg/l kanamycin. The amplified plasmid DNA was extracted by the alkaline lysis method of Birnboim, H. and J. Doly, "A rapid alkaline extraction procedure for screening recombinant plasmid DNA," Nucl. Acids Res. 7:1513 (1979) and purified by cesium chloride density gradient centrifugation (Maniatis, T. et al., "Molecular Cloning, A Laboratory Manual, Second Edition," Cold Springs Harbor Laboratory Press, Cold Springs Harbor, N.Y., pp. 142–43 (1989)). After ethanol precipitation, the plasmid was dissolved in sterile 10 mM sodium chloride to a concentration of 0.1 mg/ml.

Macroprojectiles for carrying frozen plasmid DNA during acceleration were prepared by modifying 4.5 mm caliber air gun hunting pellets (Prometheus, Inc., London, England). The metal tips of the pellets were pulled off the hollow plastic casing and discarded. One end of each ethanol-sterilized casing was pressed firmly onto the top surface of double-sided tape affixed to the inside of a petri dish, thereby forming a water-tight seal at the base of the casings.

The plasmid solution (up to 40 μl) was then pipetted into the macroprojectiles. The petri dishes containing the loaded macroprojectiles were placed on a rack above liquid nitrogen for a minimum for 15 minutes to freeze the plasmid solution.

The acceleration apparatus of the invention was precooled to 5° C. in a walk-in cold room. The stopping plate was set at 1.5 cm from the muzzle of the rifle. The agar-containing dish (onto which the filter paper-immobilized tobacco cells had been placed) was then secured upside-down on the wire scaffolding above the stopping plate so that the cells were facing the air rifle. The cells were kept at room temperature and placed in the cold room just prior to transformation.

The air rifle was then pumped ten times to provide maximum macroprojectile velocity. A macroprojectile loaded with frozen plasmid was retrieved from the liquid nitrogen container with forceps and immediately inserted into the breach of the air rifle. The plexiglass chamber was quickly fitted onto the metal base plate and a vacuum applied. When the vacuum reached 20 inches of Hg, the air rifle was fired. Typically, the time between loading the macroprojectile into the air rifle and firing was less than 10 seconds. After impact with the target, the vacuum is released, the plexiglass chamber is lifted off the metal base plate, and the target dish removed.

After transformation, the cells were left on the filter paper and incubated on the surface of the agar backing in covered petri dishes for 24 hours at 25° C. This incubation allowed time for expression of the GUS gene in the tobacco cells which were penetrated by pBI121-containing ice particles. The filter papers were then transferred to new petri dishes containing 2.5 ml of the β-glucuronidase substrate solution (Jefferson, R., "Assaying chimeric genes in plants: The GUS gene fusion system," Plant Mol. Biol. Reporter, 5:387–405 (1987)) consisting of 0.01% 5-bromo-4-chloro-3-indolyl-β-D-glucuronic acid (Clontech Laboratories, Palo Alto, Calif.), 0.2% Triton X-100, 0.5 mM potassium ferrocyanide, 0.5 mM potassium ferricyanide, and 0.1M sodium phosphate buffer (pH 7.0). The cells were incubated at 37° C. for 24 hours.

During this period, those cells transformed with and expressing the GUS gene synthesized the β-glucuronidase enzyme which catalyzed the conversion of the soluble colorless substrate to an insoluble blue product which crystallized within the cells. After fixing the cells by treatment with Farmer's fixative (75% ethanol, 25% acetic acid), the number of blue (GUS-positive) cells on the filter papers, i.e., the number of transformed cells, were counted under a dissecting microscope.

At low magnification, the primary area of impact of the frozen particles with the filter paper is clearly demonstrated by the hole in the paper which is typically 0.5–1.0 cm in diameter. The cells in this area were not recoverable. GUS-positive cells can be seen on the periphery of the hole where the velocities of the frozen particles were not high enough to penetrate the paper. Higher magnifications show the blue-stained, GUS-positive cells more distinctly.

Larger areas of blue appear to be aggregates of cells, rather than individual cells, a result observed by Klein (Klein, T. M. et al., Factors influencing gene delivery into Zea mays cells by high-velocity microprojectiles," Bio/Technology 6:559–563 (1988)) in metal spherule-mediated transformation. Untransformed cells are very slightly brownish in color or nearly transparent and cannot be seen easily against the white filter paper.

The transformation rate achieved in this experiment averaged about 55 cells per shot and was achieved at a distance of 30 mm. This required loadings of 40 μl, the maximum capacity of the macroprojectiles. The most transformants observed from a single shot under these conditions was 103 and the least was 22. High shot-to-shot variability has been noted in the other particle bombardment procedures, as well (Klein, T. M. et al., "Stable genetic transformation of intact Nicotiana cells by the particle bombardment process," Proc. Natl. Acad. Sci. USA 85:8502–8505 (1988); Oard, J. H. et al., "Transient gene expression in maize, rice, and wheat cells using an airgun apparatus," Plant Physiol. 92:334–339 (1990).

Evidence supporting the assumption that ice particles actually enter the cells comes from the observation that small pieces of ice are visible in the vacuum chamber after some shots. These pieces probably rebounded off the stopping plate, due to a slightly off-center impact with the aperture, indicating that the small volumes of ice in the macroprojectile survive acceleration and impact without thawing. An experiment similar to that outlined above, when conducted with equivalent volumes and concentrations of DNA accelerated in liquid form under the same physical conditions, results in no transformations, thereby strongly suggesting that solid ice particles, and not just accelerated liquid droplets, are required for reliable transformation.

It is now apparent that the apparatus and methods of the present invention for introducing substances into cells in a non-lethal manner show marked improvements over known apparatus and methods. It is to be understood that although certain preferred embodiments have been disclosed and described above, other embodiments are possible without departing from that which is the invention described herein. It is intended therefore that the invention be defined by the claims that follow as well as equivalents thereof.

We claim:

1. A method for genetically transforming cells comprising the steps of:
   a) preparing ice particles of a solution of copies of a DNA sequence suitable for expression;
   b) providing cells as a target;
   c) physically accelerating the ice particles containing the DNA sequence toward the cells in such a manner that at least some of the ice particles lodge in a non-lethal manner in the interior of at least some of the cells and melt to release the DNA; and
   d) confirming the existence of the DNA in the cells.

2. The method according to claim 1 wherein the solution is water-based.

3. The method according to claim 1 wherein the ice particles are formed by nebulizing the aqueous-based solution into a fine mist for such time and under such conditions sufficient to form ice particles.

4. The method according to claim 3 wherein the ice particles have diameters of less than 10 microns.

5. The method according to claim 1 wherein the ice particles are collected into and accelerated within a pellet casing.

6. The method according to claim 5 further comprising the step of providing stopping means for halting progress of the pellet casing without halting progress of the ice particles.

7. The method according to claim 6 wherein the stopping means comprises a stopping plate.

8. The method according to claim 1 further comprising the step of providing a dispersion means for scattering the ice particles prior to impact with the target.

9. The method according to claim 8 wherein said dispersion means comprises a deflector.

10. A method for genetically transforming cells comprising the steps of:

a) nebulizing a water-based solution of copies of a DNA sequence suitable for expression for such time and under conditions sufficient to produce ice particles containing the DNA;
b) collecting the ice particles into a pellet casing;
c) providing cells as a target;
d) positioning stopping means for halting the progress of the pellet casing between the pellet casing and the target;
e) positioning dispersion means for scattering the ice particles between the stopping means and the target; and
f) accelerating the pellet casing toward the target in such a manner that the pellet casing is stopped by but the ice particles pass through said stopping means, the ice particles then striking and becoming scattered by said dispersion means, such that at least some of the ice particles lodge in the target in a non-lethal manner and melt to release the DNA; and
g) confirming the existence of the DNA in the cells.

11. A method for genetically transforming cells comprising the steps of:

a) freezing a desired quantity of a solution of copies of a DNA sequence suitable for expression to form an ice block within a pellet casing;
b) providing biological material as a target;
c) positioning stopping means between the pellet casing and the target for halting the progress of the pellet casing and disrupting the integrity of the ice block into ice particles;
d) positioning between the stopping means and the target a dispersion means for scattering the ice particles;
e) accelerating the pellet casing toward the target in such a manner that the pellet casing is stopped and the ice block disrupted into ice particles by said stopping means, the ice particles then striking and becoming scattered by said dispersion means, such that at least some of the ice particles lodge in the target in a non-lethal manner and melt to release the DNA; and
f) confirming the existence of the DNA in the cells.

12. The method according to claim 11 wherein the solution is water-based.

* * * * *